(12) United States Patent
Casellas et al.

(10) Patent No.: US 8,628,770 B2
(45) Date of Patent: Jan. 14, 2014

(54) SLIMMING COSMETIC COMPOSITION CONTAINING A SUBSTANCE INDUCING THE PRODUCTION OF IL-6

(75) Inventors: Pierre Casellas, Montpellier (FR); Jean-Marie Derocq, Murviel les Montpellier (FR); Joelle Guesnet, Bures sur Yvette (FR)

(73) Assignee: Sanofi, Paris (FR)

( * ) Notice: Subject to any disclaimer, the term of this patent is extended or adjusted under 35 U.S.C. 154(b) by 1030 days.

(21) Appl. No.: 12/259,575

(22) Filed: Oct. 28, 2008

(65) Prior Publication Data

US 2009/0123455 A1    May 14, 2009

Related U.S. Application Data

(63) Continuation of application No. 11/192,845, filed on Jul. 28, 2005, now abandoned, which is a continuation of application No. 10/129,309, filed as application No. PCT/FR00/03048 on Nov. 2, 2000, now abandoned.

(30) Foreign Application Priority Data

Nov. 5, 1999 (FR) ...................................... 99 13917

(51) Int. Cl.
*A61K 35/66* (2006.01)
(52) U.S. Cl.
USPC ........................................................ 424/115
(58) Field of Classification Search
None
See application file for complete search history.

(56) References Cited

U.S. PATENT DOCUMENTS

| | | | |
|---|---|---|---|
| 3,793,153 A * | 2/1974 | Miura .............................. 435/42 |
| 5,194,259 A | 3/1993 | Soudant et al. | |
| 5,637,316 A | 6/1997 | Ribier et al. | |
| 5,827,853 A * | 10/1998 | Blanc-Ferras et al. ... 514/255.03 |
| 5,843,476 A | 12/1998 | Ribier et al. | |
| 6,114,336 A | 9/2000 | Blanc-Ferras et al. | |

FOREIGN PATENT DOCUMENTS

| | | |
|---|---|---|
| AU | 199921705 | 11/1999 |
| EP | 0 493 151 | 11/1990 |
| EP | 0 838 217 | 4/1998 |
| FR | 2 714 598 | 7/1995 |
| FR | 2 758 724 | 7/1998 |
| WO | WO 99/40896 | 8/1999 |

OTHER PUBLICATIONS

Greenberg et al. "Interleukin 6 reduces lipoprotein lipase activity in adipose tissue of mice in vivo and in 3T3-L1 adipocytes: a possible role for interleukin 6 in cancer cachexia". Cancer Res. 1992, 52(15):4113-4116.*
Wilmer et al. "Cytokine induction in human epidermal keratinocytes exposed to contact irritants and its relation to chemical-induced inflammation in mouse skin". Journal of Investigative Dermatology. 1994, 102(6): 915-922.*
Tulloch et al. "Extracellular glycolipids of *Rhodotorula* species". Canadian JOurnal of Chemistry. 1964, vol. 42, pp. 830-835.*
Derwent Patent Abstract No. 199943 (2002).
Derwent Patent Abstract No. 199836 (2002).
International Search Report WO0132137 dated May 10, 2001.

* cited by examiner

*Primary Examiner* — Vera Afremova
(74) *Attorney, Agent, or Firm* — Lathrop & Gage LLP; James H. Velema, Esq.

(57) ABSTRACT

This invention relates to a slimming cosmetic composition containing at least one compound inducing the production of IL-6 by the adipocytes in the form of a mixture with an NPY antagonist and/or an $\alpha_2$ antagonist and with an excipient for a cosmetic preparation.

3 Claims, 3 Drawing Sheets

FIG. 3A
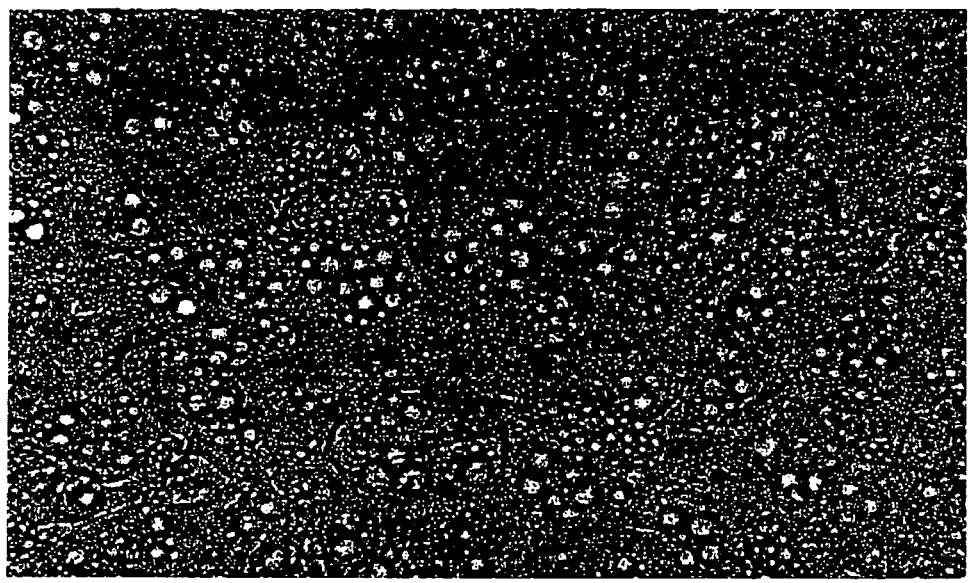
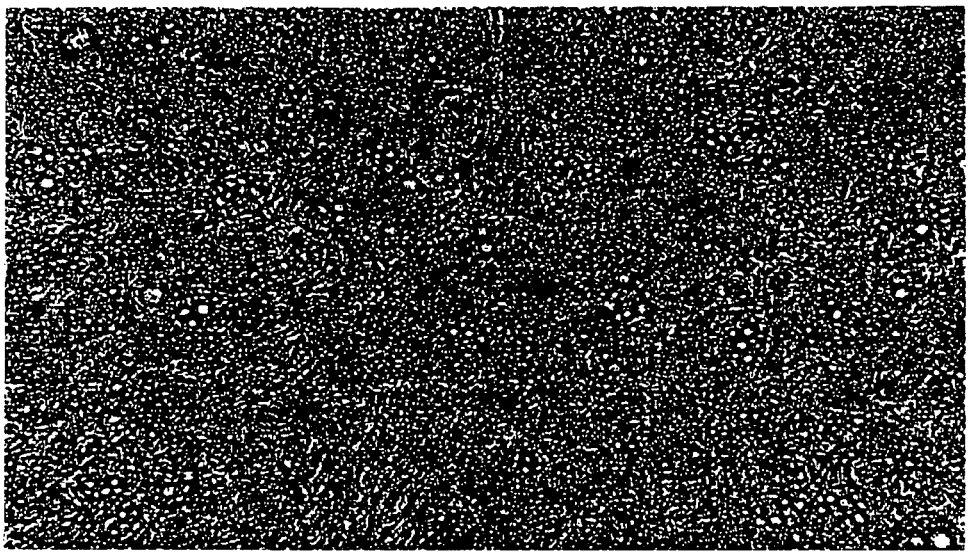
FIG. 3B

SLIMMING COSMETIC COMPOSITION CONTAINING A SUBSTANCE INDUCING THE PRODUCTION OF IL-6

The present invention relates to cosmetic compositions containing slimming active substances.

The active substances present in the cosmetic composition are chosen from an antagonist of the receptors for neuropeptide Y called hereinafter NPY, an antagonist of the α2 receptors and an inducer of the production of interleukin-6 called hereinafter IL-6.

The NPY antagonist, the α2 antagonist or the inducer of the production of IL-6 may be a nonpeptide compound, a peptide, a cell or tissue extract of animal or plant origin or a product obtained by fermentation by a microorganism, for example a bacterium or a fungus.

Patent application EP 838217 describes a slimming cosmetic composition which contains an NPY antagonist and an α2 antagonist. The active substances in this composition are obtained by fermentation by two microorganisms deposited at the Collection Nationale De Culture De Micro-Organismes (C.N.C.M.) of the Institute Pasteur at 28 rue du Dr Roux, 75724 Paris Cedex 15, France: *Streptomyces* sp. SEBR 2794 deposited Jul. 13, 1993, under the number I 1332 and *Bacillus licheniformis* SEBR 2464 deposited Oct. 22, 1996, under the number I 1778, respectively. In the present description, these active substances will be called substance A and substance B, respectively. The slimming cosmetic composition containing them will be called composition Am1.

BRIEF DESCRIPTION OF THE DRAWINGS

FIG. 3 shows the effect of substance C on the formation of lipid vesicles in the mature adipocytes 3T3-L1.

DETAILED DESCRIPTION OF THE INVENTION

Figure 1:
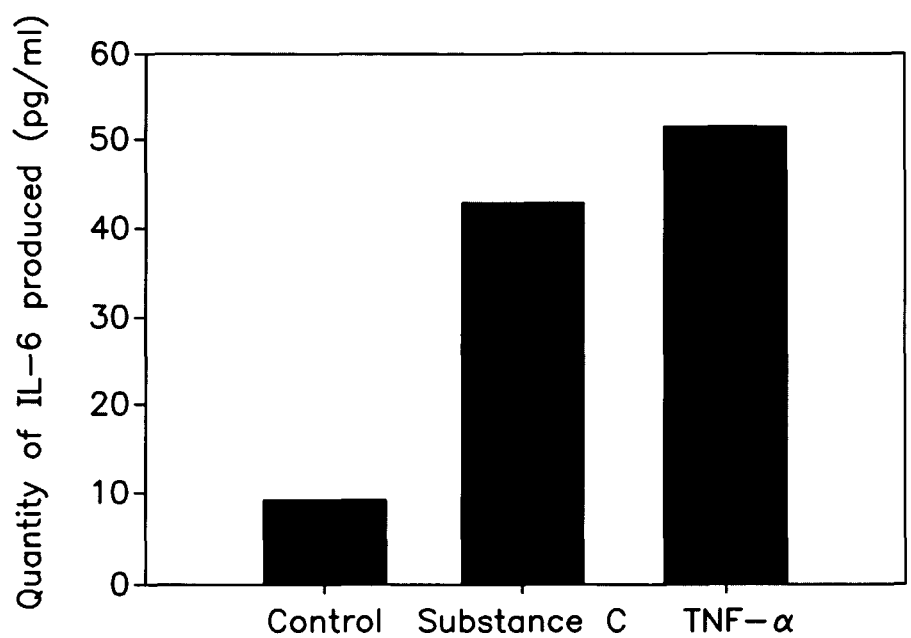
FIG. 1 shows the effect of substance C on the synthesis of adipocyte IL-6.

The preparation of substance A is described in EP 838217 and in corresponding U.S. Pat. No. 5,827,853 as follows:

The isolation of *Streptomyces* sp SEBR 2794 was carried out according to the usual method, which consists in placing a small amount of soil in suspension in distilled water, in diluting the suspension to different concentrations and in plating out a small volume of each dilution on the surface of a Petri dish containing a nutrient agar medium. After incubating for a few days at 28° C., which allows the microorganisms to grow, the various colonies are taken separately and subcultured on nutrient agar so as to obtain more abundant cultures therefrom. After culturing on nutrient agar medium and subculturing several times successively, which makes it possible to obtain an abundant and pure culture of the strain of interest, a batch 0 for storage of the parent strain is manufactured, followed by primary and secondary inoculation batches.

For this, a suspension of spores is prepared from a culture on nutrient agar medium in a Petri dish and from maintenance medium; this medium contains a cryoprotective agent making it possible to ensure good viability of the spores during conservation by freezing.

The suspension of spores obtained is divided into cryotubes which will be stored at −80° C.; these tubes constitute the batch 0.

Following the same procedure, but starting with a tube from batch 0, a primary inoculation batch is prepared.

Next, still according to the same procedure, a secondary inoculation batch is prepared from a cryotube of the primary inoculation batch.

The manufacture of the inoculation batches 0, 1 and 2 ensures long-lasting accessibility of the strain and thus of the desired activity.

*Streptomyces* sp SEBR 2794 can be cultured by any aerobic culture method. For this purpose, the various types of apparatus which are in common use in the fermentation industry are used. It is possible, in particular, to adopt the following approach for carrying out the operations.

Starting with a tube of the secondary inoculation batch, Petri dishes are seeded and, after incubating for five days, these provided a suspension of spores.

This suspension of spores is used to seed stirred conical flasks containing a suitable medium. The stirred flask can also be seeded directly with a tube of the inoculation batch. The culturing in stirred flasks can last for two to seven days but a duration of three to five days is preferred.

The production of activity is observed in the supernatant, from the first stage and onwards of culturing in flasks, but it may be advantageous to perform two successive culturing stages: a first stage for propagating the biomass, a second for production. In the latter case, a duration of one or two days is sufficient for the first stage.

The NPY receptor antagonist activity is obtained in the supernatant of the flask cultures, but it appears to be advantageous, in order to obtain a higher activity, to perform culturing in a fermenter and then to extract the supernatant therefrom. The fermenter is seeded with a one- or two-day-old stirred flask culture. In the fermenter, depending on the culture medium used, the antagonist activity may be observed in the supernatant from the first day onwards, but it is advantageous to prolong the culturing beyond three days in order to obtain an optimal production.

Culturing SEBR 2794 in a fermenter makes it possible to control better the culture conditions which are described below, such as, for example, the pH or the aeration.

The culture medium used in the fermentation process must contain at least one assimilable carbon source, an assimilable nitrogen source and mineral elements. Assimilable carbon sources which may be used are carbohydrates such as glucose, mannose, maltose, dextrins, glycerol, amino acids and proteins. Assimilable carbon sources which may also be used are acetic acid, suberic acid, citric acid, propionic acid, succinic acid and 2-ketoglutaric acid or certain animal or plant oils.

Proteins, peptones and amino acids are among the best sources of assimilable nitrogen. These sources comprise, for example, casein, lactalbumin, gluten and hydrolysates thereof, fish meal, yeast extracts and peptones.

The production of biomass may be increased by the addition, during culturing, of one and/or the other of these two main substrates.

Potassium, sodium, iron, magnesium, calcium and manganese salts are among the mineral elements added to the culture medium to ensure growth of the microorganism and to optimize the assimilation of the carbon and nitrogen sources by the cells of the microorganism, as well as phosphorus compounds such as phosphates and trace elements.

To grow the SEBR 2794 source on a medium containing these components, the process of culturing under aeration and with stirring, in which a liquid medium is used, is advantageous, although culturing on an agar medium can also be used.

The temperature, the duration of incubation, the aeration and the pH of the medium must be such that they give rise to maximum growth of the microorganism used and a maximum yield of extracts with NPY receptor antagonist activity; a culture stirred for about 2 to 7 days is usually advantageous.

The pH of the culture medium is preferably maintained at a more or less neutral or very weakly basic value and the optimum incubation temperature is between about 23° C. and 35° C., the preferred range being 25° C. to 33° C.

The culture conditions, such as the composition and pH of the medium, the incubation temperature, the stirring speed and the aeration of the fermentation may vary within a wide range and should obviously be chosen so as to obtain the best possible results.

In order to obtain extracts of the NPY receptor antagonists produced during the culturing, the supernatant is separated from the mycelium after the fermentation broth has or has not been frozen. For this separation, centrifugation, filter-press filtration or clarifying filtration, that is to say filtration in the presence of a filtering adjuvant, or any other technique usually used to extract an extracellular product from a fermentation broth can be used.

The active extract for cosmetic use is prepared from the culture supernatant obtained.

The supernatant may be concentrated by a membrane technique or by any other concentration method so as to facilitate the packaging or the use of the active solution.

Whether it has been concentrated or not, the supernatant may be diluted in various solvents which are compatible with cosmetological use.

The extract thus obtained according to this specific aspect of the present invention is filtered through a 0.2 μm filter in order to remove all trace of residual biomass and to ensure microbiological cleanliness: it is then packaged aseptically in sterile bottles and the active solution which can be used in cosmetology is obtained.

If it is desired to obtain a powder instead of an active solution, the filtrate can simply be lyophilized.

On the supernatant or the lyophilizate, the extract of the invention may be purified in a more or less thorough manner according to the conventional techniques for purifying "biomolecules," polymers, protein substances or the like, such as, for example, gel permeation chromatography, ultrafiltration, adsorption chromatography, countercurrent chromatography or electrofocalization.

The preparation of substance B is described in EP 838217 and in corresponding U.S. Pat. No. 5,827,853 as follows:

The *Bacillus licheniformis* strain SEBR 2464 was isolated as a contaminant, during experiments using columns of sand, according to the conventional microbiological techniques known to those skilled in the art.

After culturing on nutrient agar medium and subculturing several times successively, which make it possible to obtain an abundant and pure culture of the strain of interest, a batch 0 is manufactured for storage of the parent strain, followed by primary and secondary inoculation batches.

For this, a suspension of spores is prepared from a culture on nutrient agar medium in a Petri dish and from a maintenance medium; this medium contains a cryoprotective agent making it possible to ensure good viability of the spores during storage by freezing.

The suspension of spores obtained is divided into cryotubes which will be stored at −80° C.: these tubes constitute batch 0.

Following the same procedure, but starting with a tube from batch 0, a primary inoculation batch is prepared.

Next, still according to the same procedure, a secondary inoculation batch is prepared from a cryotube of the primary inoculation batch.

The manufacture of the inoculation batches 0, 1 and 2 ensures long-lasting accessibility of the strain and thus of the desired activity.

The *Bacillus licheniformis* SEBR 2464 can be cultured by any aerobic culture method and in various types of apparatus usually used in the fermentation industry. It is possible, in particular, to adopt the following approach for carrying out the operations.

Starting with a tube of the secondary inoculation batch, Petri dishes are seeded and, after incubating for two days, these allow stirred conical flasks containing a suitable medium to be inoculated.

A stirred flask can also be seeded directly with a tube of the inoculation batch. In this case, the duration of culturing will be longer for the same medium.

The antagonist activity is obtained in the flask cultures within 10 hours to 48 hours depending on the culture conditions used.

The α2-receptor antagonist activity may be obtained by extracting the supernatant of the flask cultures, but it appears to be advantageous, in order to obtain a higher activity, to perform culturing in a fermenter and then to extract the supernatant therefrom.

The fermenter is seeded with a 1- to 2-day-old culture in a stirred flask; it is preferable for the culture not to have begun to sporulate.

In the fermenter, according to the culture conditions used, the antagonist activity may be observed from the first hours of culturing and onwards, but it is advantageous to wait until the stationary growth phase has been reached before extracting.

Culturing SEBR 2464 in a fermenter allows better control of the culture conditions which are described below, for example the pH and the aeration.

The α2-receptor antagonist activity obtained in the fermenter may vary, depending on the culture conditions applied.

The characteristics of the medium are identical to those described above for the strain SEBR 2794.

In order to grow the strain SEBR 2464 on a medium containing these components, the process of culturing under aeration and with stirring, in which a liquid medium is used, is advantageous, although culturing on an agar medium can also be used.

The temperature, the duration of incubation, the aeration and the pH of the medium must be such that they give rise to a maximum growth of the microorganism used and a maximum yield of extract with α2-receptor antagonist activity.

A culture stirred and aerated for about 10 hours to 48 hours is usually advantageous.

The pH of the culture medium is preferably maintained at a more or less neutral or very weakly acidic value and the optimum incubation temperature is between 25° C. and 50° C.

The culture conditions, such as the composition and pH of the medium, the incubation temperature, the stirring speed and the aeration of the fermentation, may vary within a wide range and should obviously be chosen so as to obtain the best possible results.

The production of an extract having a high α2-receptor antagonist activity requires several extraction steps.

A first step consists in eliminating the biomass. For this, centrifugation, tangential microfiltration, clarifying filtration, that is to say a filtration in the presence of a filtering adjuvant, or any other method usually used to extract an extracellular product from a fermentation broth may be used. The supernatant is then placed in contact overnight with a hydrophobic resin preferably made of polystyrene-divinylbenzene, for example such as Amberlite XAD$_2$ resin (Rohm & Haas) or CHP20P resin (Mitsubishi).

The loaded resin is then separated by frontal filtration and the filtrate is removed.

The resin undergoes several successive extractions with different solvents, allowing molecules of a hydrophobic nature to be extracted. After each extraction, the resin is separated from the organic phase by filtration.

The various organic phases are then evaporated under vacuum, together or separately, until one or more dry extracts are obtained.

The dry extract thus obtained may be taken up in various solvents usually used in cosmetology.

The uptake concentration is chosen to allow complete dissolution of the extract and to be compatible with the subsequent use. In order to eliminate all trace of residual biomass and to ensure its microbiological stability, the extract is filtered on a 0.2 µm filter and divided aseptically into sterile flasks.

This slimming composition Am1 acts on the subcutaneous adipose tissue and controls the release of the fat stored in the adipocytes.

By blocking the $\alpha 2$ and NPY receptors, composition Am1 makes it possible to clear the hypertrophied adipocytes and to avoid any new excessive adipocyte storage by allowing the expression of the $\beta$ receptors whose prolipolytic activity is normally masked by the antilipolytic $\alpha 2$ and NPY receptors which are largely in excess in the subcutaneous adipose tissues. Composition Am1 thus makes it possible to act effectively on the outflow of the fatty acids stored in the adipocytes.

The compositions according to the present invention maintain this activity but supplement it, on the one hand, by a retarding action on the entry of fatty acids which exerts itself by a reducing effect on the production of LPL, the enzyme responsible for the entry of fatty acids into the cell and, on the other hand, on the hyperplasia of the adipocytes. This unexpected supplementary effect is obtained by a substance capable of inducing the production of IL-6 by the adipocytes. This substance is produced by a microorganism, *Rhodotorula* sp SEBR 2002, deposited on Feb. 11, 1997, at the Collection Nationale De Culture De Micro-Organismes (C.N.C.M.) of the Institute Pasteur at 28 rue du Dr Roux, 75724 Paris Cedex 15, France, registered under the reference I 1844. This active substance will be called hereinafter substance C.

For long considered solely for their role as energy reserve, the adipocytes have demonstrated during the past few years endocrine and secretory cell functions (Ailhaud G. et al. Médecine/Science 1998, 14, 858-864). Leptin perfectly illustrates this new secretory function of the adipocyte. This protein is specifically produced by the mature adipocyte. It is involved in controlling satiety; it is also thought to be involved in the regulation of fatty deposits. The adipocyte is thus responsible for the production of factors with autocrine and paracrine activity which will modulate the physiology of the adipose tissue.

In particular, it has been very recently demonstrated that the endocrine function of the adipocyte is exerted on two specific mediators:
  lysophosphatidic acid (LPA), a lipid factor whose production is mediated by the activation of the $\alpha 2$ receptor and whose function consists in recruiting new adipocytes (Valet P. et al. J. Clin. Invest. 1998, 101(7), 1431-1438).
  IL-6, which is a multifunctional cytokine.

Substance C is known as an inducer of the production of IL-6 by the keratinocytes. It exerts an effect on skin aging.

The method of production of substance C is described in published international patent application WO 99/40896 as follows:

The isolation of the yeast strain *Rhodototula* sp, deposited under the number I 1844, was carried out by following the conventional method which consists in diluting a small amount of water of the sample to various concentrations, and in spreading a small volume of each dilution onto the surface of a Petri dish containing a nutrient agar medium. After a few days of incubation at 28° C., which enables the microorganisms to develop, the various colonies are individually sampled and subcultured on nutrient agars in order to obtain more abundant cultures thereof.

After culturing on nutrient agar medium and several successive subculturings which make it possible to obtain an abundant and pure culture of the strain of interest, a conservation batch 0 of the stock strain, and then primary and secondary seed batches, are manufactured.

For this, a yeast suspension is prepared starting from a Petri-dish culture on a nutrient agar medium and using a recovery medium; this medium contains a cryoprotector for ensuring good viability of the microorganism during the conservation by freezing.

The obtained yeast suspension is distributed into cryotubes, which are conserved at −80° C.: these tubes constitute batch 0.

Following the same protocol, but starting from a tube of batch 0, a primary seed batch is prepared.

Then, still according to the same protocol, a secondary seed batch is prepared starting from a cryotube of the primary seed batch.

The manufacture of seed batches 0, 1 and 2 insures long-lasting access to the strain and thus to the desired activity.

The culturing of the strain I 1844 can be carried out by any aerobic culture method. For this purpose, various types of machines are used which are commonly used in the fermentation industry. The following approach can in particular be adopted for carrying out the procedures.

Using the secondary seed batch, Petri dishes are seeded which, after incubation for two to three days, provide a yeast suspension which is used to seed stirred Erlenmeyer flasks containing a suitable medium. The stirred flask can also be directly seeded with a tube of the seeding batch. The stirred-flask culturing can last from one to three days.

The production of activity is observed by extracting the obtained biomass by filtration or centrifugation with organic solvents.

Right from the first culture step in flasks, it may be advantageous to carry out two successive culture steps: a first step for multiplying the cells and propagating the biomass, and a second for the production. In this latter case, a duration of one to two days is sufficient for the first step.

The desired activity can be obtained by extracting the biomass of the flask cultures, but, in order to obtain the desired activity in greater amount, it appears to be advantageous to prepare a fermenter culture and then to extract its biomass.

The fermenter is seeded with a 1- to 2-day-old stirred flask culture; it is preferable for the culture still to be in the exponential phase.

In a fermenter, depending on the culture conditions used, the activity may be observed right from the first hours of culture, but it is advantageous to wait for the stationary growth phase to be reached before proceeding with the extraction. The fermenter culturing of I 1844 makes it possible to better control the culture conditions which are described below, for example the pH and the aeration.

The culture medium used in the fermentation method should contain at least one source of carbon which can be assimilated, one source of nitrogen which can be assimilated and mineral elements. As sources of carbon which can be assimilated, use may be made for example of carbohydrates such as glucose, mannose, maltose, dextrins, glycerol, amino acids and proteins.

As sources of carbon which can be assimilated, use may also be made of acetic, suberic, citric, propionic, succinic and 2-ketoglutaric acids, or animal or plant oils.

The best sources of nitrogen which can be assimilated are to be found among proteins, peptones and amino acids. These sources comprise, for example, casein, lactalbumin and gluten, and the hydrolysates thereof, fish meal, yeast extracts or peptones.

The biomass production can be increased by adding, during culturing, one or the other of these two principal substrates.

Among the mineral elements added to the culture medium to ensure microorganism growth and to optimize the assimilation of the carbon and nitrogen sources by the cells of the microorganism, mention may be made of potassium, sodium, iron, magnesium, calcium or manganese salts, as well as phosphorus compounds such as phosphates and trace elements.

The culture is stirred and aerated for a duration which varies between 10 hours and 60 hours, which makes it possible to obtain advantageous results.

Preferably, the pH of the culture medium is maintained at a slightly acid value and the optimum incubation temperature is between 23° C. and 38° C., the preferred range being 25° C. to 33° C.

The culture conditions such as the composition and pH of the medium, the incubation temperature, the stirring speed and the fermentation aeration may vary within broad limits, and are chosen so as to obtain the best possible results.

The production of the active extract requires several extraction steps.

A first step consists in separating the biomass from the rest of the must; for this, it is possible to use centrifugation, tangential microfiltration, rotary drum filtration or any other method conventionally used by persons skilled in the art to separate the biomass from a fermentation must. The biomass is then brought into contact for a few hours with a mixture of solvents which makes it possible to extract molecules of hydrophobic nature.

The preferred duration of bringing into contact is overnight, i.e. approximately 15 hours.

The biomass and the loaded organic phase are then separated by frontal filtration, and the biomass is discarded.

The organic phase is then evaporated off under vacuum at a temperature ranging from room temperature to 50° C. until a dry extract is obtained.

The dry extract thus obtained can be taken up in various solvents conventionally used in cosmetology.

The uptake concentration is chosen so as to allow complete dissolution of the extract and so as to be compatible with subsequent use.

In order to remove any trace of residual biomass and to ensure its microbiological stability, the extract is filtered through a membrane with a 0.2 μm exclusion threshold, and distributed aseptically into sterile flasks. The aseptic preparation of these solutions makes it possible to avoid adding a preservative.

Nothing could indicate that this substance (produced by the microorganism I 1844) would moreover have exerted a double action on the adipocytes.

Recently, studies have shown that the adipose cells could produce IL-6 whose function at the adipocyte level consists in repressing the synthesis of LPL, the enzyme responsible for the entry of fatty acids into the adipose cell (Greenberg A. S. et al. Cancer Research 1992, 52, 4113-4116).

The production of IL-6 by the cells of the subcutaneous adipose tissue is positively correlated with an increase in the body mass index (Mohamed Ali V. et al. J. Clin. Endocrinol. Metab. 1997, 82, 4196-4200) but also differs according to the origin of the adipose tissue.

Thus, in obese subjects, the basal adipocytes collected from the omental region releases 2 to 3 times more IL-6 than the subcutaneous adipocytes (Fried S. K. et al. J. Clin. Endocrinol. Metab. 1998, 83, 847-860).

Finally, in addition to the capacity of IL-6 to reduce the production of LPL by the adipocytes, IL-6 could also act, through inhibition, on the differentiation of the adipocyte-precursor cells (Hauner H. et al. 8th International Congress on obesity 1999, 47-53).

IL-6 therefore appears as a cytokine which has an autocrine action (on LPL) and a paracrine action (on the preadipocytes) for slowing down the development of the subcutaneous adipose tissue.

However, like all cytokines, IL-6 is a pleiotropic glycoprotein, that is to say that it exhibits different effects depending on the cell producing it. Thus, at the level of the adipocyte, IL-6 will have effects of a completely different type to those already known with the keratinocyte.

In particular, in the adipocyte, the IL-6 synthesized by the cell down-regulates the content and therefore the activity of the enzyme which is responsible for the entry of fats.

Thus, the compositions according to the invention make it possible to control the phenomena of entry and outflow of fatty acids including storage and hypertrophy of the adipocytes. It also makes it possible to act on adipocyte hyperplasia.

It is known that the formation of new adipocytes occurs in humans throughout the life of the individuals. Thus, "dormant" fatty cells have been isolated in elderly subjects whatever their gender (Ailhaud G. et al. Int. J. Obes. Relat. Metab. Disord. 1992, 16(2), 517-521; Spiegelman B et al. Cell 1996, 87, 377-389; Hauner et al. J. Clin. Invest. 1989; 84, 1663-1670).

The development of the adipose tissue results from an increase in the size of the adipocytes following the excessive accumulation of fatty acids, as well as from the recruitment of new fatty cells obtained from the multiplication and differentiation of adipocyte-precursor cells, the preadipocytes (Valet P. et al. J. Clin. Invest. 1998, 101(7), 1431-1438).

This recruitment of new adipocytes is mediated by soluble factors produced by the hypertrophied adipocytes: in particular by LPA via the stimulation of the α2 receptor, and by IL-6 via its controlling power on preadipocyte differentiation.

The blocking of the α2 receptor is therefore such as to allow, in parallel with its beneficial effect on lipolysis, repression of the release of LPA, with, as advantage, an inhibition of the recruitment of new adipocytes.

IL-6 limits the maturation of the preadipocytes into differentiated adipocytes. The adipocyte stimulation of the production of this cytokine by the inducer of IL-6 reinforces this property.

The combination of substance B, inhibitor of the receptor, and of substance C, inducer of IL-6, is therefore such as to allow an increased and innovative efficacy on the hyperplasia of the fatty cells. The addition of substance A to this combination makes it possible to obtain a slimming composition which acts on several mechanisms of action, namely hypertrophy and hyperplasia.

Studies have been carried out to demonstrate the activity of the active substance obtained from the microorganism I 1844, or substance C, on the mature adipocytes and on the adipocyte differentiation.

A slimming cosmetic composition has now been prepared, according to the invention, which contains substances A, B and C and which will be called hereinafter Am2.

The slimming effect of Am2 has been the subject of clinical studies.

The biological effects of substance C in vitro has been studied on the murine line 3T3-L1. This preadipocyte line, routinely cultured in DMEM medium (Dubelco's Minimum Essential Medium) enriched with 10% foetal calf serum has the property of differentiating into mature adipocytes in the presence of inducers such as insulin and indomethacin (Slieker L. J. Biochem. Biophys. Res. Com. 1998, 251, 225-229). Eight to ten days after the induction of differentiation, the 3T3-L1 cells exhibit the characteristics of mature adipocytes. This passage from the stage of immature cell to the stage of functional adipocyte can be morphologically assessed by the appearance of intracytoplasmic lipid storage vesicles which are visible under the microscope or which can be biochemically detected by measuring the production of leptin, the hormone for satiety produced solely by mature adipocytes.

The influence of substance C on the adipocyte activity was evaluated at two levels. On the one hand, by measuring the capacity of this active agent to modulate the production of adipocyte IL-6 and, on the other hand, by evaluating its effect on differentiation into mature adipocytes.

1—Effect of Substance C on the Production of IL-6 by the Mature Adipocytes 3T3-L1

Mature adipocytes 3T3-L1 (harvested after 10 days of differentiation induced by the insulin (5 µg/ml) and indomethacin (125 µm) combination) are stimulated with substance C at 1% (v/v) for 24 hours. The culture supernatant is then removed and its IL-6 content measured by ELISA (Enzyme Linked Immunosorbent Assay) according to the supplier's instructions (R&D Systems, Abingdon, GB). The quantity of IL-6 secreted is compared with that of a control culture treated only with the solvent for substance C (ethanol/water (50/50) mixture, diluted 1/100 in the culture medium) and of a culture stimulated with a reference IL-6 inducer, TNF-α. at 50 ng/ml (Fried S. K. J. Clin. Endocrinol. Metab. 1998, 83, 847-860). FIG. 1 shows that substance C stimulates the production of IL-6 from the adipocytes 3T3-L1 by a factor of about 5 compared with the solvent control culture (43 pg/ml against 9 pg/ml respectively), that is 83% of the effect obtained with the reference inducer (52 pg/ml).

The results obtained show that, on the one hand, substance C recognizes the adipocytes as induction target and that, on the other hand, under the effect of substance C, the basal production of IL-6 by the adipocytes is increased by a factor of 5, that is 83% of the maximum effect obtained with the positive control.

Such an increase makes it possible, taking into account the known properties of IL-6, to envisage, in a first instance, a reduction of the synthesis of the enzyme charged with the entry of the fatty acids, LPL, and then following that, a reduction in the entry of the fatty acids.

2—Effect of Substance C on Adipocyte Differentiation

The objective of this second study was to identify the effects of substance C on the formation of new adipocytes.

The influence of substance C on the differentiation of the preadipocytes 3T3-L1 into mature adipocytes is studied, on the one hand, by evaluating the synthesis of the hormone leptin, a marker of adipocyte differentiation, and, on the other hand, by observing under the microscope the formation of intracytoplasmic lipid vesicles, other indicators of the functional transformation into mature adipocytes. In all cases, substance C is introduced into the culture at 1% (v/v) at the beginning of the differentiation process (induced as above) and maintained up to its end. The synthesis of leptin is evaluated every two days by ELISA assay (R&D Systems, Abingdon, GB).

Figure 2:
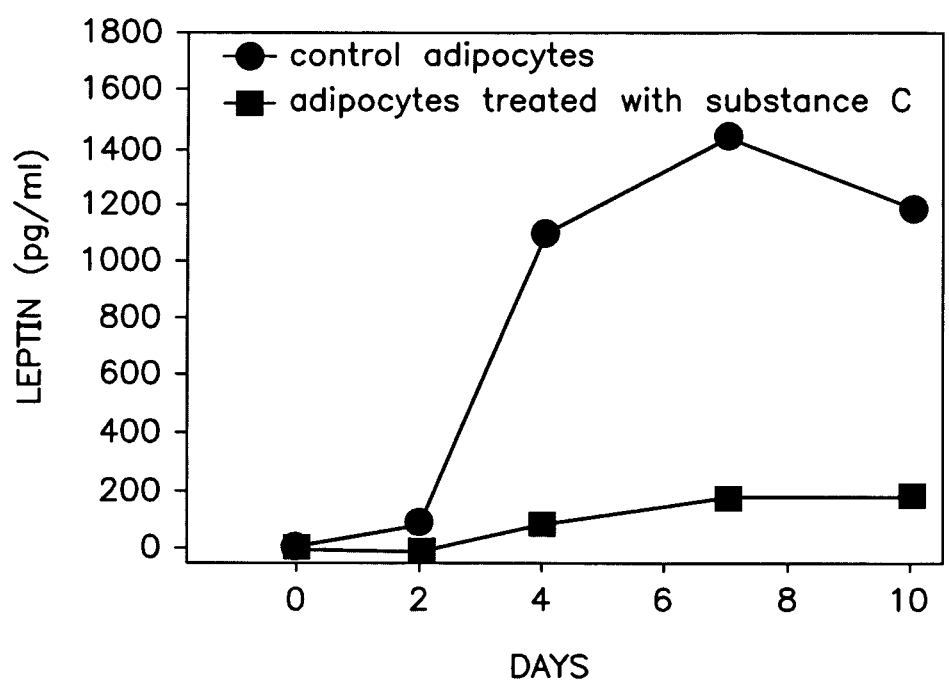
FIG. 2 shows the effect of substance C on adipocyte differentiation.

FIG. 2 shows that in the presence of substance C, the production of leptin remains at an extremely low level throughout the 10 days of the experiment and is markedly lower (≤200 pg/ml) than that observed in the control culture which, as expected, sees its leptin level increase from the 2nd day following the induction of differentiation, and increases up to a maximum plateau of 1200-1400 pg/ml from the 6th day. The inhibition of the synthesis of leptin by substance C constitutes the first parameter for the blocking of the adipocyte differentiation process.

The second is provided by the experiment shown in FIG. 3 which indicates that after 10 days of differentiation, the control cells develop a morphology of mature adipocytes containing large lipid vesicles which occupy practically the entire cytoplasmic space (A), whereas the same cells treated with substance C remain at a very immature stage with a few rare vesicles which are much smaller in size (B).

Using the 3T3-L1 model, commonly used in the literature for the exploration of adipocyte functions, it has been demonstrated that substance C has the dual property of stimulating, in mature adipocytes, the production of IL-6 and of inhibiting, in precursor cells, the transformation into mature adipocytes. Substance C therefore acts upstream by preventing adipocyte maturation and downstream by stimulating, at the level of the mature adipocytes, the production of a cytokine which is involved in limiting the storage of fatty acids.

These results support the unique property of the substance to induce the production of IL-6 by the adipocytes whose autocrine function (on the producing cells) and paracrine function (on the cells in the vicinity of the producing cells) is exerted both on the entry of fatty acids into the mature adipocytes, and on the recruitment of new adipocytes, by a termination of the differentiation of the preadipocytes.

Preliminary clinical studies have been carried out with slimming compositions according to the invention which contain the 3 active substances (hereinafter called composition Am2).

Two clinical studies were carried out with composition Am2.

The first relates to the measurement of the thickness of the subcutaneous adipose tissue, and the second uses the centimetric measurement.

1) Measurement of the Thickness of the Subcutaneous Adipose Tissue

The objective of this study is to evaluate the clinical efficacy of the novel composition Am2 containing the 3 active substances.

The protocol used is described below.

Number of subjects: 61 healthy female volunteers, divided into 2 groups (31 subjects using the slimming composition Am2 containing the 3 active substances, 30 subjects the slimming composition Am1).

The products are applied twice per day over the whole of the thighs by a circular massage which is stopped after complete penetration of the product.

The evaluation of the efficacy was determined over a period of 2 months by measuring the thickness of the subcutaneous adipose tissue at $T_0$, $T_{28\ days}$, $T_{56\ days}$. The method used is that of echography.

The site for the measurement is identified by a skin marking and by the height at which the probe is positioned.

To facilitate the vertical identification and to avoid any movement or compression of the tissues during the measurement, the echographic probe is placed on a stable device, which can be adjusted in height and independently of the operator.

Three images are acquired successively at the level of the identification mark. On each image, 3 measurements of thickness are performed. All the 6 measurements thus obtained make it possible to obtain a precision of $\pm 1$ mm.

These measurements are supplemented with monitoring of the weight of the subjects included in the trial and with an analysis of the self-evaluations.

The significance of the results are evaluated by means of Student's t test for paired groups. The test is applied to the raw values as well as to the variation of these parameters over the duration of the trial (value expressed in terms of $T_0$).

Regardless of the group considered, the average weight remained stable during the entire duration of the study and is not therefore likely to be responsible for the variation in the measurement of the thickness of the subcutaneous adipose tissue of the thighs.

The study conditions selected do not make it possible to confirm a significant slimming effect for composition Am1: after 1 month of application, a reduction of 0.8% of the subcutaneous adipose tissue is observed and at 2 months a reduction of 2.6% is observed.

Composition Am2 makes it possible to obtain a very significant slimming effect from the 28th day of application ($p<10^{-5}$): the reduction in the subcutaneous adipose tissue observed with composition Am2 is $-2.2\%$ at 1 month and $-4.3\%$ at 2 months of application.

1) Centimetric Measurement

The protocol below was used.

Number of subjects: 39 female volunteers divided into 2 groups: 20 received composition Am1 and 19 composition Am2.

The products are applied twice per day for 2 months.

The evaluation of the slimming efficacy was evaluated by centimetry at $T_0$, $T_{28\ days}$ and $T_{56\ days}$ at the level of the thighs (at 3 cm below the buttock fold), on the right and on the left.

Regardless of the group considered, the average weight is substantially constant during the entire duration of the study and is not therefore likely to be responsible for the variations in the measurement of the thickness of the subcutaneous adipose tissue of the various regions studied.

Table 1 presents the significant results obtained by centimetry.

| COMPOSITION | % of subjects | | Reduction range | |
| --- | --- | --- | --- | --- |
| | 1 month | 2 months | 1 month | 2 months |
| Composition Am1 | 30 | 45 | 1-2.0 cm | 1-2.0 cm |
| Composition Am2 | 72 | 73 | 1-3.5 cm | 1-2.5 cm |

Composition Am2 has a better slimming activity versus $T_0$ than composition Am1, from one month of application.

Comparison of the results obtained following these two studies makes it possible to identify the marked superiority of composition Am2 over its placebo, and also reveals the better performance of composition Am2 compared with composition Am1.

Thus, although sharing part of the mode of action through substances A+B and their efficacy on lipolysis, the intensity of the beneficial effects obtained with the novel formula Am2 is reinforced by virtue of the action of substance C on the entry of fatty acids into the adipocytes.

The combination of these effects, backed by the activity on the recruitment of new adipocytes, makes it possible to reduce the importance of the existing adipose tissue and to prevent its development.

In the preparation of the compositions according to the present invention, the extracts thus constituted are mixed with aqueous or nonaqueous solvents and with conventional diluents which are compatible with a topical use as well as with the active components of the same composition. Appropriate solvents and/or diluents will be chosen according to their capacity to transport the active component of the extract of the invention into the subcutaneous adipose layer.

These compositions generally contain excipients or additives chosen from the ingredients usually used in compositions intended for local application depending on the requirement of the particular formulations envisaged.

They may contain, for example, thickening agents, demulcents, emollients, stabilizers, preservatives, antifoaming agents, surfactants, antioxidants, colorants and/or pigments, and perfumes.

They may also contain other active components which have either an effect of the same type, for example products which contribute to the regulation of lipolysis/lipogenesis or products useful in this type of topical composition such as stimulators of the synthesis of collagen, inhibitors of collagenase or of elastase, and vasoprotective agents.

The cosmetic compositions of the present invention contain substances A, B or C in proportions of between 0.00001% and 5% relative to the total weight of the composition, in the form of a mixture with the excipients commonly used for the preparation of cosmetic formulations to be applied to the skin.

The said proportions may vary in the range indicated above depending on the intrinsic activity of the components included in the composition. Preferably, components A, B and C are present in proportions of 0.0001% to 2%.

An advantageous form of the compositions according the invention is a fluid which is topically applied by means of an adhesive support, designated hereinafter "patch", this patch allowing controlled diffusion of the active components.

The compositions of the present invention have good stability and can be preserved for the period necessary for use at temperatures between 0° C. and 60° C. without there being sedimentation of the constituents or separation of the phases, or a reduction in activity which can compromise their use.

These compositions are very well tolerated; they exhibit no phototoxicity and their application to the skin, for prolonged periods, involves no side effect.

From the first applications, the skin relief is smooth; the skin becomes more tonic and firm. After applying for one month, the slimming effect appears, the "orange skin" appearance visibly diminishes and the figure becomes slimmer.

The present application claims benefit to prior applications PCT/FR00/03048, and U.S. Ser. No. 10/129,309 and 11/192,845, the entire contents of each of which are hereby incorporated by reference.

EXAMPLE 1

Slimming Composition in the Form of a Spray Patch

| Raw materials | Quantity % by weight |
|---|---|
| Demineralized water | qs 100 |
| Covacryl AC (sodium polyacrylate) | 0.8 |
| Covacryl RM (sodium polyacrylate) | 1.4 |
| PVP K30 (PVP) | 0.2 |
| Covacryl A15 (acrylate copolymers) | 7 |
| Covacryl E14 (acrylate copolymers) | 3 |
| Covaplast (acetyltributyl citrate/triethyl citrate/trioctyl trimellitate/ethyl lactate | 2.5 |
| Simusol 98 (Oleth-20) | 0.5 |
| Dermosoft octiol (ethylhexanediol) | 0.5 |
| Substance A | 0.14 |
| Substance B | 0.007 |
| Substance C | 0.5 |
| Propellant gas (butane) | |

EXAMPLE 2

Slimming Composition in the Form of a Spray Patch

| Raw materials | Quantity % by weight |
|---|---|
| Demineralized water | qs 100 |
| CMC 7 LF (cellulose gum) | 0.5 |
| Natrosol 250 HX (hydroxethylcellulose) | 0.3 |
| Aquatrix part B (water and carboxymethylchitosan and paraben) | 13 |
| Demineralized water 20 | 20 |
| Aquatrix part A (demineralized water and PVP) | 13 |
| Phenonip (phenoxyethanol, methylparaben, propylparaben, butylparaben, ethylparaben) | 1 |
| Simulsol 98 (Oleth-20) | 1 |
| Substance A | 0.08 |
| Substance B | 0.004 |
| Substance C | 0.25 |
| Propellant gas (butane) | |

EXAMPLE 3

Slimming Composition in the Form of a Gel

| Raw materials | Quantity % by weight |
|---|---|
| Demineralized water | qs 100 |
| Trilon B (tetrasodium EDTA) | 0.2 |
| Carbopol 2980 (carbomer) | 0.5 |
| Glycerin | 3.0 |
| Demineralized water | 20 |
| Lubragel MS (polyglyceryl metacrylate and propylene glycol) | 5.0 |
| Dipropylene glycol | 3.0 |
| Butylene glycol | 5.0 |
| Phenonip (phenoxyethanol, methylparaben, propylparaben, butylparaben, ethylparaben) | 0.65 |
| Triethanolamine | 0.5 |
| Substance A | 0.10 |
| Substance B | 0.01 |
| Substance C | 0.1 |

EXAMPLE 4

Slimming Composition in the Form of an Emulsion

| Raw materials | Quantity % by weight |
|---|---|
| Demineralized water | qs 100 |
| Triethanolamine | 0.85 |
| Lanette 16 (cetyl alcohol) | 0.5 |
| Miglyol 812 (caprylic/capric triglyceride) | 2.5 |
| Stearine TP (stearic acid) | 1.5 |
| Super Hartolan (lanolin alcohol) | 0.2 |
| Silicon DC 200 fluid (dimethicone or simethicone SI RAL) | 0.5 |
| Generol 122N (soyabean glycine) | 1.0 |
| Tegin (glyceryl stearate SE) | 1.0 |
| Myglyol 840 (propylene glycol dicaprylate/edicaprate) | 7.0 |
| Eutanol G (alcohol) | 1.5 |
| Montane 60 (Sorbitan stearate) | 0.43 |
| Montanox 60DF (Polysorbate 60) | 0.57 |
| Carbopol 981 2% solution (carbomer) | 13.0 |
| Butylene glycol | 6.0 |
| Phenonip (phenyoxyethanol, methylparaben, propylparaben, butylparaben, ethylparaben) | 1.0 |
| DL-α-tocopherol acetate (tocopheryl acetate) | 0.1 |
| Substance A | 0.02 |
| Substance B | 0.001 |
| Substance C | 0.3 |

EXAMPLE 5

Slimming Composition in the Form of an Emulsion Gel

| Raw materials | Quantity % by weight |
| --- | --- |
| Water | qs 100 |
| Trilon B (tetrasodium EDTA) | 0.03 |
| Natrosol 250 HX (hydroxyethylcellulose) | 0.25 |
| Pemulen TR-1 (acrylate copolymer) | 0.20 |
| Butylene glycol 1.3 pure | 5 |
| Dipropylene glycol | 3 |
| Triethanolamine | 0.2 |
| Phenonip (phenoxyethanol, methylparaben, propylparaben, butylparaben, ethylparaben) | 1 |
| DC 2502 (cetyldimethicone) | 4 |
| Dermol 105 (isodecyl neopentanoate) | 3 |
| Sodium hyaluronate | 0.01 |
| Veragel liquid 1:1 (*Aloe barbadensis* gel) | 1 |
| Substance A | 0.15 |
| Substance B | 0.1 |
| Substance C | 0.05 |

The invention claimed is:

1. A slimming cosmetic composition comprising three components:
   1) a neuropeptide Y (NPY) antagonist component purified from an extract obtained by fermentation by the *Streptomyces* sp. strain deposited at the C.N.C.M. of Institut Pasteur under the number I-1132;
   2) an $\alpha_2$ antagonist component purified from an extract obtained by fermentation by the *Bacillus licheniformis* strain deposited at the C.N.C.M. of Institut Pasteur under the number I-1778; and
   3) a component inducing production of interleukin-6 (IL-6) by adipocytes that is purified from an extract obtained by fermentation by the *Rhodotorula* sp. strain deposited at the C.N.C.M. of Institut Pasteur under the number I-1844,
   said components in a mixture along with an excipient for cosmetic preparations.

2. A slimming cosmetic composition for topical application comprising:
   1) a neuropeptide Y (NPY) antagonist purified from an extract obtained by fermentation by the *Streptomyces* sp. strain deposited at the C.N.C.M. of Institut Pasteur under the number I-1132;
   2) an $\alpha_2$ antagonist purified from an extract obtained by fermentation by the *Bacillus licheniformis* strain deposited at the C.N.C.M. of Institut Pasteur under the number I-1778;
   3) an inducer of the production of IL-6 by adipocytes, said inducer purified from an extract obtained by fermentation by the *Rhodotorula* sp. strain deposited at the C.N.C.M. of Institut Pasteur under the number I-1844; and
   4) a cosmetically acceptable excipient.

3. A method for regulating lipolysis/lipogenesis in the skin comprising administering to a subject a composition of claim 1 or 2.

* * * * *